United States Patent [19]
Venkateshwaran et al.

[11] Patent Number: 5,912,009
[45] Date of Patent: Jun. 15, 1999

[54] FATTY ACID ESTERS OF GLYCOLIC ACID AND ITS SALTS

[75] Inventors: Srinivasan Venkateshwaran; David Fikstad, both of Salt Lake City; Sonal R. Patel, Sandy, all of Utah

[73] Assignee: TheraTech, Inc., Salt Lake City, Utah

[21] Appl. No.: 08/959,944

[22] Filed: Oct. 29, 1997

Related U.S. Application Data

[63] Continuation-in-part of application No. 08/741,071, Oct. 30, 1996, abandoned.

[51] Int. Cl.⁶ ........................................................ A61F 13/02
[52] U.S. Cl. ............................ 424/448; 424/447; 424/449
[58] Field of Search ..................................... 424/448, 447, 424/449; 514/772, 785, 946

[56] References Cited

U.S. PATENT DOCUMENTS

| | | |
|---|---|---|
| 3,472,931 | 10/1969 | Stoughton . |
| 3,551,154 | 12/1970 | Di Blas et al. . |
| 3,728,447 | 4/1973 | Osipow et al. . |
| 3,742,951 | 7/1973 | Zaffaroni . |
| 3,797,494 | 3/1974 | Zaffaroni . |
| 4,006,218 | 2/1977 | Sipos . |
| 4,164,190 | 8/1979 | Newman . |
| 4,198,311 | 4/1980 | France et al. . |
| 4,422,952 | 12/1983 | Koulbanis et al. . |
| 4,568,343 | 2/1986 | Leeper et al. . |
| 4,761,279 | 8/1988 | Khalil et al. . |
| 4,820,720 | 4/1989 | Sanders et al. . |
| 4,822,601 | 4/1989 | Goode et al. . |
| 4,849,224 | 7/1989 | Chang et al. . |
| 4,855,294 | 8/1989 | Patel et al. . |
| 4,863,970 | 9/1989 | Patel et al. ............................. 514/784 |
| 4,888,354 | 12/1989 | Chang et al. . |
| 4,940,586 | 7/1990 | Cheng et al. . |
| 4,960,814 | 10/1990 | Wu et al. . |
| 4,973,468 | 11/1990 | Chiang et al. . |
| 4,983,395 | 1/1991 | Chang et al. . |
| 5,006,342 | 4/1991 | Cleary et al. . |
| 5,093,112 | 3/1992 | Birtwistle et al. . |
| 5,122,383 | 6/1992 | Heiber et al. . |
| 5,152,997 | 10/1992 | Ebert et al. . |
| 5,154,122 | 10/1992 | Goldschmidt . |
| 5,212,199 | 5/1993 | Heiber et al. . |
| 5,227,169 | 7/1993 | Heiber et al. . |
| 5,302,395 | 4/1994 | Ebert et al. . |
| 5,314,694 | 5/1994 | Gale . |
| 5,427,772 | 6/1995 | Hagan . |
| 5,601,839 | 2/1997 | Quan et al. ............................. 424/488 |
| 5,609,875 | 3/1997 | Hadas .................................. 424/195.1 |

FOREIGN PATENT DOCUMENTS

| | | |
|---|---|---|
| 9505153 | 2/1995 | WIPO . |
| 96/02903 | 2/1996 | WIPO . |
| 96/37231 | 11/1996 | WIPO . |

OTHER PUBLICATIONS

Dohi et al., *Enhancing Effects of Myristyl Lactate and Lauryl Lactate on Percutaneous Absorption of Indomethacin*, Pharm. Bull. 2877–2897 (1990).

Kaiho, et al., *Enhancing Effect of Letyl Lactate on the Percutaneous Absorption of Indomethacin in Rats.* Chem. Pharm. Bull. 37(4) 1114–1116 (1989).

Murphy et al. *Acyl Lactylates in Cosmetics* (1969).

Murphy et al. *Sorption of Acyl Lactylates by Hair and Skin as Documented by Radio Tracer Studies,* Toiletries 43–49 (1979).

Osipow et al., *Fatty Acid Lactylates,* D&CL. Mar. & May, 1969.

*Primary Examiner*—Thurman K. Page
*Assistant Examiner*—Lakshmi Channavajjala
*Attorney, Agent, or Firm*—Thorpe, North & Western

[57] ABSTRACT

A transdermal drug delivery system which enhances the delivery of the drug comprises a composition containing, as an enhancer, one or more $C_6$ to $C_{22}$ fatty acid esters of glycolic acid and its salts. These compositions are made up of a safe and effective amount of an active pharmaceutical permeant contained in a penetration-enhancing vehicle comprising, 0.25 to 50% w. of the fatty acid glycolic acid ester enhancer in a suitable carrier vehicle. These fatty acid glycolic acid ester enhancers may be used in various carrier vehicles to enhance the transdermal delivery of active permeants in either free form or used in an occlusive device, particularly in a transdermal patch in matrix or reservoir form. When used in matrix patch form, the fatty acid glycolic acid ester enhancers and permeants are incorporated into a biocompatible adhesive. When used in a reservoir type patch, the permeant and fatty acid glycolic acid ester enhancers are incorporated into a carrier fluid of controlled viscosity such as a gel or ointment preferably containing a lower alkanol and water. In free form, the enhancer and permeant may be incorporated into an ointment, lotion, cream, or similar formulation.

40 Claims, No Drawings

FATTY ACID ESTERS OF GLYCOLIC ACID AND ITS SALTS

This application is a continuation-in-part of application Ser. No. 08/741,071 filed October 30, 1996, now abandoned.

FIELD OF THE INVENTION

The present invention relates to the use of fatty acid esters of glycolic acid and its salts as permeation enhancers. More particularly, this invention relates to the use of esters of one or more fatty acids and glycolic acid and salts thereof as permeation enhancers for the transdermal delivery of a wide range of active permeants.

BACKGROUND OF THE INVENTION AND DESCRIPTION OF PRIOR ART

The transdermal administration of drugs is becoming increasingly accepted as a preferred mode of delivery.

Transdermal delivery of drugs provides many advantages over conventional oral administration. Advantages of transdermal systems include convenience, noninterrupted therapy, improved patient compliance, reversibility of treatment (by removal of the system from the skin), elimination of "hepatic first pass" effect, the high degree of control over blood concentration of any particular drug and consequent reduction of side effects.

Although transdermal systems have many advantages, most drugs are not amenable to this mode of administration due to the well known barrier properties of the skin. Molecules moving from the environment into and through intact skin must first penetrate the stratum corneum and any material on its surface. The molecule must then penetrate the viable epidermis, the papillary dermis, and then the capillary walls and into systemic circulation. Along the way, each of the above mentioned tissues will exhibit a different resistance to penetration by the same molecule. However, it is the stratum corneum that presents the greatest barrier to absorption of topical compositions or transdermally administered drugs. The stratum corneum, the outer horny layer of the skin, is a complex structure of compact keratinized cell remnants separated by lipid domains. Compared to the oral or gastric mucosa, the stratum corneum is much less permeable to outside molecules.

The flux of a drug across the skin can be increased by changing either a) the resistance (the diffusion coefficient), or b) the driving force (the solubility of the drug in the stratum corneum and consequently the gradient for diffusion). Many enhancer compositions have been developed to change one or more of these factors, and are known in the art. U.S. Pat. Nos. 4,006,218, 3,551,154 and 3,472,931, for example, respectively describe the use of dimethylsulfoxide (DMSO), dimethyl formamide (DMF) and N,N-dimethylacetamide (DMA) to enhance the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

The use of sorbitan esters of long chain aliphatic acids as skin permeation enhancers is disclosed in U.S. Pat. Nos. 5,122,383; 5,212,199 and 5,227,169. Skin permeation enhancement using aliphatic alcohol esters of lactic acid is disclosed in U.S. Pat. No. 5,154,122, World Patent 95/09006 and in Dohi et al., *Enhancing Effects of Myristyl Lactate and Lauryl Lactate on Percutaneous Absorption of Indomethacin*, Chem Pharm. Bull. 38 (October 1990) 2877–2879. U.S. Pat. No. 5,314,694 also makes reference to the use of esters of fatty acid alcohols, i.e. lauryl alcohol and lactic acid as a permeation enhancer component.

World Patent 96/37231 teaches the use of acyl lactylates as permeation enhancers for drug delivery purposes. This patent is specific to esters of fatty acids and lactic acid such as caproyl lactylic acid and lauroyl lactylic acid. It is stated that the salt form of acyl lactylates are not effective as permeation enhancers.

Skin permeation enhancement due to fatty acid sucrose esters is disclosed in U.S. Pat. No. 4,940,586. Penetration enhancement resulting from combining free base and acid addition salt combinations of drugs is taught in U.S. Pat. No. 4,888,354. Enhancement of drugs by means of subsaturation in a carrier is disclosed in U.S. Pat. No. 5,164,190.

Occlusive adhesive devices, i.e. patches, for transdermal delivery of drugs is taught in U.S. Pat. Nos. 4,849,224; 4,983,395; 5,152,997 and 5,302,395. These patches are in reservoir or matrix forms as will be more fully characterized in the detailed description below.

Many of the enhancer systems possess negative side effects such as toxicity, skin irritation and incompatibility with the drugs or other ingredients making up the transdermal system.

U.S. Pat. No. 4,855,294 discloses compositions for reducing skin irritation caused by drug/enhancer compositions having skin irritation properties comprising a percutaneously absorbable drug, a binary enhancer composition consisting of a solvent and a cell envelope disordering compound, combined with an amount of glycerin sufficient to provide an anti-irritating effect.

It would be desirable to have an enhancer composition which not only enabled the passage of drug compositions across the skin barrier but which was also beneficial to the moisturization, stability and overall vitality of the epidermis. Skin having properly moisturized stratum corneum is smooth to the touch, flexible and elastic due to the presence of sufficient bound water. A 1% variation of water content may be enough to modify skin elasticity and permeability. Suitable skin hydration also promotes transdermal delivery of drugs through the stratum corneum.

Fatty acid lactylates and glycolates are known to be used as hair conditioners as shown by U.S. Pat. No. 3,728,447. Further, fatty acid lactylates and their salts, prepared from $C_6$ to $C_{22}$ fatty acids, are known to be used in cosmetics and have the ability to complex with skin proteins. See Murphy, et al., *Acyl Lactylates in Cosmetics*, D&CI (May, 1978) 35 ff and Murphy, et al., *Sorption of acyl lactylates by hair and skin as documented by radio tracer studies*, Cosmetics & Toiletries, 94 (March 1979) 43–49. Combinations of acyl lactylates or glycolates with soaps or synthetic detergents in skin conditioning toilet bars is the subject of U.S. Pat. No.

4,198,311. The use of a salt of a fatty acid ester of lactylic acid as one of many components in a shaving cream formulation is taught in U.S. Pat. No. 4,761,279.

Lanolinyl lactylates, are shown in U.S. Pat. No. 4,422,952 to be used in water-in-oil emulsions as cosmetic supports or pharmaceutical excipients, e.g. to be used in ointments, balms, creams and the like. No physiological effect is attributed to these esters.

U.S. Pat. No. 4,822,601 is drawn to cosmetic base compositions exhibiting therapeutic properties including sucrose fatty acid esters and fatty acid lactylates, with or without shea butter. Following application to the skin, a thickening of the epidermal layer was noted indicating a healthier and less dry skin. It was noted that topical application of such compositions also demonstrated enhanced wound healing properties and decreased sensitivity to UV light.

Extensive summaries of the prior art for acyl lactylates and of the properties of such for cosmetic use are found in U.S. Pat. No. 5,427,772 and World Patent 96/37231.

In none of the above is the use of fatty acid esters of glycolic acid and its salts as permeation enhancers for active pharmaceutical agents taught, suggested or demonstrated.

OBJECTS AND BRIEF SUMMARY OF THE INVENTION

Accordingly, it is an object of the present invention to provide a composition for enhancing the transdermal delivery of drugs which has good skin tolerability and presents minimal risks of skin toxicity or irritation.

It is still another object of the invention to provide a composition for the transdermal administration of drugs containing, as an enhancer, one or more $C^6$ to $C^{22}$ fatty acid esters of glycolic acid and its salts.

Another object of the invention is to provide a method of enhancing the transdermal delivery of a variety of drugs having either or both hydrophobic and hydrophilic characteristics using one or more $C_5$ to $C_{21}$ fatty acid esters of glycolic acid and its salts as an enhancer.

These and other objects may be realized by means of a composition for transdermal delivery consisting of a broad category of pharmaceutically-active agents which are lipophilic or hydrophilic, including salts, and which produce minimal or no skin irritation to human or animal tissue systems. The invention provides penetrating transdermal compositions based on the use of a pharmaceutically-active agent dissolved in, or admixed with, a penetration-enhancing amount of one or more $C_6$ to $C_{22}$ fatty acid esters of glycolic acid or its salts as more fully described below, in a suitable carrier vehicle such as a member selected from the group consisting of a biocompatible pressure sensitive adhesive and a fluid, e.g. a suspension, emulsion or solution, of controlled viscosity. Suitable pressure sensitive adhesives will be subsequently described. Fluids of controlled viscosity include water, optionally containing a lower alkanol. Also, other inert ingredients which are soluble within the enhancer composition may be utilized in the place of water in forming fluids of any desired viscosity. Such fluids may be single phase, e.g. solutions, or phase separated systems such as suspensions or emulsions. The continuous phase forming such liquids can vary from hydrophilic to hydrophobic depending upon the desired combination.

The drug enhancer combination is preferably contained in a device, preferably an occlusive device, for purposes of holding the composition against the skin or mucosa surface for administration. Such devices are generally patches for adhesion to the skin surface and may be in either matrix or reservoir form.

The invention is therefore not limited to any specific category or categories of permeants, but is inclusive of all therapeutically active compounds, and their uses to which they are responsive as more fully set forth herein. The invention is also inclusive of mixtures of permeants which may be administered simultaneously.

Also, the invention is drawn to treatment methods by means of which an effective amount of a permeant, combined with the enhancer system, is applied to the skin of a human or animal subject.

While the combination of permeant and fatty acid esters of glycolic acid and its salts in a delivery system is not limited to any particular format or composition, delivery patches in liquid reservoir or matrix forms are preferred. Such patches may or may not contain an occlusive backing. Also, the simple application of a drug enhancer combination applied to the skin in free form as a viscous fluid such as a cream, gel, or ointment are all within the scope of the invention. The only limitation is that the composition must be effective for its intended use.

DETAILED DESCRIPTION OF THE PREFERRED EMBODIMENTS

The following definitions will be useful in describing the invention and will eliminate the need for repetitive explanations.

When used in context, the terms "enhancement", "penetration enhancement" or "permeation enhancement" relates to an increase in the permeability of the skin to a drug, so as to increase the rate at which the drug permeates through the skin. The enhanced permeation effected through the use of such enhancers can be observed, for example, by measuring the rate of diffusion of the drug through animal or human skin using a diffusion cell apparatus. The diffusion cell is described by Merritt et al. Diffusion Apparatus for Skin Penetration, *J. of Controlled Release*, 1 (1984) pp. 161–162.

By "transdermal" delivery, is meant transdermal or percutaneous administration, i.e., delivery by passage of drug through the skin. Hence the terms "skin", "derma", "epidermis", and the like shall also be used interchangeably unless specifically stated otherwise.

By "afflicted situs" is meant a localized area of pathology, discomfort, infection, inflammation or lesion, and the immediately surrounding area.

By "application situs" is meant a site suitable for topical application with or without the means of a mechanical sustained release device, patch or dressing, e.g., behind the ear, on the arm, back chest, stomach, leg, top of foot, etc.

"Carriers" or "vehicles" as used herein refer to carrier materials suitable for transdermal drug administration, and include any such materials known in the art, i.e., any liquid gel, solvent, liquid diluent, adhesive, or the like, which is nontoxic and which does not interact with other components of the composition in a deleterious manner. Carriers, which also may function as solvents in some instances, are used to provide the compositions of the invention in their preferred form. Examples include, but not limited to, water, ethanol, propanol, isopropanol, mineral oil, silicone oil, polyethylene glycol, polypropylene glycol, liquid sugars, waxes, petroleum jelly and a variety of other oils and polymeric materials along with adhesive materials such as polyacrylate, silicone, natural and synthetic rubbers or other adhesives.

By the term "permeant" or "drug" is meant any chemical material or compound suitable for transdermal administration which includes a desired biological or pharmacological effect by topical application to the "affliction situs" or by systemic delivery from the "application situs". Such substances include the broad classes of compounds normally delivered through body surfaces such as the skin. In general, this includes therapeutic agents in all of the major therapeutic areas including, but not limited to, anti-infectives such as antibiotics and antiviral agents, analgesics and analgesic combinations, anorexics, antidiarrheal, antihistamines, anti-inflammatory agents, antimigraine preparations, antimotion sickness agents, antinauseants, antineoplastic, antiparkinsonism drugs, antipruritic, antipsychotic, antipyretics, antispasmodics including gastrointestinal and urinary, anticholinergic, sympathomimetic, xanthine derivatives, cardiovascular preparations including calcium channel blockers, beta-blockers, antiarrythmics, antihypertensives, diuretics, vasodilator including general coronary, peripheral and cerebral, central nervous system stimulants including cough and cold preparations, decongestants, diagnostics, hormones, immunosupressives, muscle relaxants, parasympatholytic, parasympathomimetic, psychostimulants, sedatives and tranquilizers. The term "permeant" is also meant to include mixtures. By mixtures is meant combinations of permeants from different categories, mixtures of permeants from the same category and mixtures of free base and salt forms of the same or different permeants from the same or different categories.

By "effective" amount of a drug or permeant is meant a nontoxic but sufficient amount of a compound to provide the desired local or systemic effect. An "effective" amount of permeation enhancer as used herein means an amount selected so as to provide the desired increase in transdermal permeability and, correspondingly, the desired depth of penetration, rate of administration and amount of drug. By "effective" amount of fatty acid ester of glycolic acid or its salts or any other enhancer or carrier component, e.g. lower alkanol or glycerin, is meant the amount found beneficial in a particular delivery system to achieve the desired delivery of the drug from the system.

By "drug delivery system", "drug/enhancer composition" or any similar terminology is meant a formulated composition containing the drug to be transdermally delivered in combination with such "carriers" or "vehicles", penetration enhancers, excipients, or any other additives.

By the term "matrix", "matrix patch" or "matrix system" is meant an active permeant homogeneously combined in a biocompatible pressure sensitive adhesive which may or may not also contain other ingredients or in which the enhancer is also homogeneously dissolved or suspended. A matrix system is usually an occlusive adhesive patch having an impermeable film backing and, before transdermal application, a release liner on the surface of the adhesive opposite the film backing. A matrix system therefore is a unit dosage form of a drug composition in an adhesive carrier, also containing the enhancer and other components which are formulated for maintaining the drug composition in the adhesive in a drug transferring relationship with the derma or skin. Adhesive patches having non-occlusive backings are also considered to be within the scope of this definition unless specifically excluded.

By "fluid of controlled viscosity" is meant a vehicle or carrier in which the permeant, enhancer and solvent, along with any other additives, are contained in a single or phase separated fluid state. The fluid per se may serve as a solvent or a solvent or co-solvent may be added. Such fluids can be water or organic based and may contain a mixture of liquids or solvents appropriately gelled or thickened. In other words, such fluids may comprise, but are not limited to, solutions, suspensions, emulsions, gels, ointments, creams, pastes or any other similar state which permits the outward diffusion of the permeant and enhancer and, optionally, a solvent or other additives as desired.

By the term "reservoir", "reservoir patch" or "reservoir system" is meant an active permeant combined in a fluid of controlled viscosity contained in an occlusive device having an impermeable back surface and an opposite surface configured appropriately with permeable membranes and adhesives for transdermal application. A reservoir system therefore is a unit dosage form of a drug composition in a fluid carrier of controlled viscosity, also containing the enhancer and other components which is formulated in an occlusive device for maintaining the drug composition in the carrier in a drug transferring relationship with the derma or skin.

By "free form" is meant a gel, lotion, cream, paste, ointment and the like containing an active permeant combined in a fluid of controlled viscosity in which the enhancer is also dissolved or suspended and which may be applied directly to an afflicted situs.

The compositions of this invention require, at a minimum, a permeant capable of producing systemic effects, or producing or possessing local activity, in a carrier vehicle containing, as an enhancer, a fatty acid ester of glycolic acid or a salt thereof. Such carrier vehicle may be a pressure sensitive adhesive or fluid of controlled viscosity. Such fluids may be water based and contain a $C_2$ or $C_3$ alcohol with or without other optional ingredients within suitable ranges. However, solvents or liquids other than water may also be used as a base fluid phase. In addition, the fatty acid esters of glycolic acid or a salt thereof may be combined with other enhancers, such as cell envelope disordering compounds and solvents other than water and $C_2$ and $C_3$ alcohols.

Cell envelope disordering compounds are known in the art as being useful in topical pharmaceutical preparations. These compounds are thought to assist in skin penetration by disordering the lipid structure of the stratum corneum cell-envelopes. A representative listing of these compounds is described in the patents cited in the prior art section above which are incorporated herein by reference.

For purposes of definition herein, cell-envelope disordering compounds and solvents other than water, ethanol, propanol and isopropanol shall be referred to as "secondary enhancers". This is an arbitrary definition for use in this disclosure as such "secondary enhancers" are known in the art to function as sole or primary enhancers.

Glycolic acid and its salts that are useful the preparation of esters are those represented by the formula:

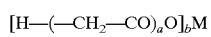

where a is an integer of 1 to 4, b is 1 or 2 and M is H or a pharmaceutically acceptable counterion having a valency of 1 or 2. When M is other than H, any pharmaceutically acceptable counterion having a valency of 1 or 2 may be utilized in salt formation. Alkali, alkaline earth, ammonium and amine salts are suitable counterions. Representative of these are alkali metal salts such as sodium and potassium; alkaline earth metal salts such as magnesium and calcium and ammonium and amine salts. The amines may be primary, secondary or tertiary and may be alkyl, aryl, alkaryl and aralkyl amines wherein the aliphatic terms are as those defined above. By alkyl and alkenyl is meant any straight or branched, saturated or unsaturated, chain having from 1 to 22 carbon atoms and by aryl is meant any carbocyclic or heterocyclic group having properties of aromaticity.

Fatty acids used in the preparation of esters are those represented by the formula RCOOH, where R is a $C_5$ to $C_{21}$ alkyl or alkenyl chain which may be either straight or branched chained and which may contain hydroxy substituents. Straight $C_8$ to $C_{18}$ alkyl, alkenyl or hydroxy substituted alkyl or alkenyl chains are preferred. Representative of saturated acids, where R is alkyl, are caproic acid, caprylic acid, capric acid, lauric acid, myristic acid, palmitic acid, stearic acid, and the like. Representative of unsaturated acids, where R is alkenyl, are palmitoleic acid, oleic acid, linoleic acid, linolenic acid, ricinoleic acid, arachidgnic acid and the like. Mixtures of acids, including mixtures of saturated and unsaturated acids may also be used.

The fatty acid esters of glycolic acid and its salts may be represented by the formula:

$$[RCO-(O-CH_2-CO)_aO]_bM$$

where R, M, a and b are as represented above. Preferably M is a member selected from the group consisting of H, Na, K, Ca, Mg and ammonium or amines salts. Since these fatty acid esters of glycolic acid and glycolic acid salts are described in the prior art, further definition is not necessary. These compounds, sometimes also described as acyl glycolates are available from R.I.T.A. Corporation (Woodstock, Ill.).

Particularly preferred fatty acid esters of glycolic acid and its salts are members selected from the group consisting of lauroyl glycolate, caproyl glycolate, cocoyl glycolate, isostearoyl glycolate, sodium lauroyl glycolate, tromethamine lauroyl glycolate and the like.

The fatty acid esters of α-hydroxy acid when used as enhancers, may be present in an enhancer/carrier system in amounts ranging from between about 0.25 to 50% w. The effective amount of enhancer may vary depending on whether the delivery composition is for use in a reservoir or free form composition or a matrix patch and may vary depending on any number of factors such as the hydrophilic/hydrophobic properties of the drug, drug concentration, whether the enhancer is used in free acid or salt form, the particular matrix or reservoir components, etc. In all systems ranges of between about 0.25 and 30% w are preferable. Most preferably the enhancer content will range between about 0.5 to 15% w regardless of the particular system.

The bulk of the enhancer/carrier system is preferably an adhesive, in the case of a matrix device, or a mixture of lower alkanol, preferably ethanol or isopropanol, and inert carrier, preferably water, with or without a gelling agent, in the case of a reservoir or free form composition.

In the reservoir or free form systems the enhancer will generally be present in the enhancer/carrier system in ranges of between about 0.25 and 50% w with ranges of between about 0.25 and 30 being preferable and ranges of between about 0.5 to 15% w being most preferable.

In such systems, the concentration of water may be present in amounts of between about 0 to 99% w. When water is present, the range may vary between about 1 and 99% w with ranges of between about 5 to 50 percent being preferred. The lower alcohol content may vary between about 0 and 89% by weight of the enhancer/carrier system. When alcohols are present the range may vary between about 1 and 89% w with alcohol concentrations of between about 30 and 65% w. being most preferred.

Gelling or thickening agents will also preferably be utilized in the reservoir or free form compositions. These may be present in amounts ranging from between about 0.5 to 20% by weight with ranges between about 0.5 and 5% being preferred.

Additionally, glycerin may be added as an anti-irritant or to modulate the delivery of the active permeant and may be present in amounts of from 0 to 60% by weight. When used, glycerin is present in amounts of between about 1 and 60% with amounts of 10 to 50% by weight being preferred.

Free form compositions, for application directly to an afflicted situs as a gel or ointment, may be similar in content to the reservoir formulations for containment in an occlusive device.

Suitable thickening agents include hydrophilic polymers such as hydroxypropyl cellulose, hydroxypropyl methylcellulose, hydroxy ethylcellulose, ethylcellulose, carboxymethyl cellulose, dextran, gaur-gum, polyvinylpyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and the like.

In matrix systems the adhesive is present in amounts ranging from 50 to 99.75% by weight and will preferably be present in amounts of between about 70 and 99.5% by weight. The enhancer is also homogeneously dissolved or suspended in the adhesive matrix and is present in amounts of between about 0.25 and 50% by weight with ranges of between about 0.5 to 30% w being preferred and 0.5 to 15% w being most preferred.

In the matrix systems the carrier is primarily the pressure sensitive adhesive in which the enhancer and an effective amount of an active permeant or drug are homogeneously combined.

Suitable pressure sensitive adhesives may include acrylic copolymer adhesives or "acrylic adhesive", (e.g. National Starch Durotak 80-1196, National Starch Nacor 72-9965 and Monsanto Gelva 737), rubber based adhesives or "rubber adhesive", such as polyisobutylene or "PIB adhesive", (e.g. Adhesive Research MA-24), ethylene-vinylacetate copolymer adhesives or "EVA adhesive" (e.g. National starch EVA-TACK 33-4060), styrene butadiene rubber adhesives or "SBR adhesives", (e.g. National Starch Nacor 72-8725) and silicone based adhesives or "silicone adhesive", (e.g. Dow Bio-PSA). However, any other suitable pressure sensitive adhesives may also be used which are compatible with the active permeant and enhancer when utilized.

The cell envelope disordering compounds as secondary enhancers may be present in the enhancer/carrier in amounts that do not add to the overall enhancer content as designated above. Rather, part of the fatty acid esters of glycolic acid or a salt thereof, or primary enhancer, is replaced by the secondary enhancer such that the weight ratio of primary enhancer to secondary enhancer is between about 5:1 to 1:3 with ratios of between about 2:1 to 1:2 being preferred and ratios of about 1:1 being most preferred.

Preferred secondary enhancers or cell-envelope disordering compounds are members selected from the group consisting of methyl laurate, lauryl alcohol, glycerol monolaurate, oleic acid, oleyl alcohol, glycerol monooleate, glycerol dioleate and glycerol trioleate and mixtures thereof.

Suitable solvents, other than or in addition to water, ethanol, propanol and isopropanol include diols, such as propylene glycol and glycerol; $C_4$–$C_{10}$ mono-alcohols; DMSO, dimethylformamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

Preferred solvents are members selected from the group consisting of a $C_3$ or $C_4$ diol, DMSO, DMF, DMA, 1-n-dodecylcyclazacycloheptan-2-one. N-methyl-pyrrolidone and N-(2-hydroxyethyl)pyrrolidone and mixtures thereof.

Provided there is no negative effect on the functionality of the formulation, the drug delivery composition may, in addition, include one or more carriers, vehicles, or excipients, and various agents and ingredients commonly employed in dermatological and cosmetic gels, creams and ointments or other preparations. Examples are, but not limited to, fragrances, pacifiers, preservatives, anti-oxidants, emollients, oils, stabilizers, coloring agents and the like.

It will be appreciated by those skilled in the art that relative amounts of the other components in these compositions can vary greatly. For example, the amount of drug present in a given composition will depend upon a variety of factors, including but not limited to, the disease or condition to be treated, the nature of the drug, the activity of the drug, the desired effect, the situs of application, possible adverse reactions, the cost and availability of the drug, solubility of the drug, and other factors within the particular knowledge of the patient and physician.

The method of application of the present invention may vary within limits, but necessarily involves applying the selected drug composition to the skin or other tissue where drug delivery is initiated and continues at a relatively sustained rate for a period of time sufficient to provide the desired pharmacological or biological response. When applied to an "afflicted situs" the method may involve a gel, lotion, cream, ointment, or the like. When applied to an "application situs" for systemic the method may involve the use of a drug delivery system device as taught, for example, in U.S. Pat. Nos. 3,742,951, 3,797,494, 4,568,343, 4,849,224 or 4,983,395. Alternatively, in suitable situations, drug delivery system devices may also be applied to an "afflicted situs".

In either event the reservoir or matrix device is brought in contact with the skin at the application situs and is held in place on the skin at the application situs by a suitable adhesive. In the reservoir device, the drug enhancer composition may be applied to the skin through a permeable membrane forming the reservoir floor which is in diffusional contact with the skin.

It is to be understood that while the invention has been described in conjunction with the preferred specific embodiments thereof, that which follow are intended to illustrate and not limit the scope of the invention. Other aspects of the invention will be apparent to those skilled in the art to which the invention pertains.

Experimental

The following experiments relate to combinations of a pharmaceutically active substance and a fatty acid ester of either a glycolate in which the transdermal permeation of the active substance is shown to be substantially increased by the presence of glycolate fatty acid esters. The examples given below illustrate the transdermal permeation enhancing effect of these enhancers for acidic, basic, and non-ionic drugs, though it is understood that the invention will not be limited to the drug substances contained in these examples.

Adhesive Matrix Preparation

Pressure sensitive adhesive matrix systems were prepared according to the following steps. First, the solids content of the adhesive solution (water or organic solvent based) was determined by placing a known weight of solution in a weighed aluminum dish and evaporating the solvents overnight in a 70° C. convection oven. The solid adhesive content of the solution was calculated by dividing the adhesive solid weight after drying by the initial total solution weight. Next, a weighed quantity of adhesive solution was added to a glass bottle and the drug substance, permeation enhancer, and other excipients were weighed and added to the adhesive solution in a quantity necessary to achieve the desired dry matrix film composition. The solution containing the adhesive polymer, drug substance, and other excipients as necessary was then mixed overnight. After mixing, approximately 8 ml of the solution was dispensed on a silanized polyester release liner and film cast using a casting knife with a gap size appropriate to achieve a final dried thickness of approximately 0.05 mm. The cast film was dried in a 70° C. convection oven until all solvents had evaporated to yield a dried matrix (15 minutes for organic solvent based adhesives, 30 minutes for water emulsion based adhesives). Finally, an 0.08 mm thick occlusive polyethylene backing film was laminated onto the dried adhesive matrix, and these systems were then used to conduct in vitro skin flux experiments as described below.

Reservoir or Free Form Hydroalcoholic Gel Preparation

Hydroalcoholic gels were prepared on a 10 ml scale as follows. Ethyl alcohol (190 proof ethanol), water, glycerin, enhancer and drug were combined in the appropriate proportions and mixed for several hours. The gelling agent (e.g. carbomer) was added and the solution was mixed briefly at high shear, then mixed at low shear until a gel was formed.

Skin Flux Studies

In vitro skin flux studies were conducted using human cadaver epidermal membrane in modified Franz non-jacketed diffusion cells. The epidermal membrane (stratum corneum and epidermis) was separated from whole skin (epidermal membrane and dermis) by the method of Kligman and Christopher (*Arch. Dermatol.* 88:702 (1963)). This method involves the exposure of the full-thickness skin to water at 60° C. for a time period of 60 seconds. After this period, the epidermal membrane was gently peeled off the dermis and stored for later use in aluminum foil at −5° C.

Prior to each permeation experiment with a matrix system, the matrix system was cut into a circular sample of 0.7 $cm^2$ area and the silanized release liner was removed. The adhesive was affixed to the stratum corneum side of the thawed epidermal membrane which was then cut to an appropriate size and clamped in place between the two halves of the diffusion cell with the stratum corneum facing the donor compartment. The receiver compartment was filled with water or an aqueous solution appropriate to maintain sink conditions for the drug. All receiver solutions included 0.02% (w/w) sodium azide ($NaN_3$) to inhibit bacterial growth. The diffusion cell was placed in a temperature controlled circulating water bath calibrated to maintain the surface temperature of the skin at 32° C. The receiver compartment was constantly stirred by a magnetic stir-bar in the receiver compartment agitated by a magnetic stirring module placed under the water bath.

Permeation experiments with hydroalcoholic gels were performed using both finite occluded doses and thin unoccluded films. The occluded dose is an appropriate in vitro model for the application of a transdermal patch drug delivery system containing a liquid or gel reservoir, while the thin unoccluded film is an in vitro model for free form topical application.

Occluded dosing experiments were set-up according to the following procedure. Prior to skin permeation experiments, the epidermal membrane was cut to an appropriate size and placed between the two halves of the diffusion cell with the epidermal side facing the receiver compartment. The receiver compartment was filled with an appropriate solution then the diffusion cell was placed in a circulating water bath calibrated to maintain the temperature of the skin surface at 32° C. and allowed to hydrate overnight. After hydration, a sample of the gel (75 μl) was pipetted into a cavity created by placing a polyethylene washer over the stratum corneum surface. This cavity was covered with an occlusive backing film which was clamped in place.

Thin film unoccluded dosing experiments with hydroalcoholic gels were set-up using the following procedure adapted from Chiang et al. (*Int J. Pharm.* 49: 109–114 (1989)). The stratum corneum side of a piece of epidermal membrane was attached to one side of an adhesive-coated metal shim with a circular hole of 0.64 cm² area cut in the center. The epidermal side of the membrane-metal shim assembly was kept overnight on Whatman filter paper saturated with an appropriate receiver solution in order to hydrate the membrane.

After hydration the membrane-shim assembly was placed epidermal side down on a flat glass surface. A small sample of the formulation to be tested (about 20 μl) was dispensed into the central cavity of the shim and a flat glass plate was used to spread the gel evenly in the annular space in the center of the shim and to remove the excess gel. The gel remaining on the skin after this procedure is completed forms a thin film with a total volume of 7 μl over the 0.64 cm² skin surface area (equivalent to a dose of 11 μl/cm² which is typical for free form topical applications). The membrane-shim assembly is then clamped in place on a temperature-controlled diffusion cell as described above with the epidermal side of the membrane facing the receiver compartment.

The following sampling procedure was used for all dosage forms. At predetermined sampling time points, the entire contents of the receiver compartment were collected for drug quantitation and the receiver compartment was filled with fresh solution, taking care to eliminate any air bubbles at the skin/solution interface. The cumulative amount of drug permeated per unit area at any time t($Q_t$, μg/cm²) was determined as follows:

$$Q_t = \sum_{N=0}^{t} (C_N * V)/A$$

where $C_N$ is the concentration (μg/ml) of the drug in the receiver sample for the corresponding sample time, V is the volume of fluid in the receiver chamber (~6.3 cm³), and A is the diffusional area of the cell (0.64 cm²).

EXAMPLE 1

Permeation enhancement of estradiol with lauroyl glycolic acid was compared to permeation enhancement using the known permeation enhancer, lauroyl lactylic acid, as disclosed in World Patent 96/37231. Estradiol at 1.5% (w/w) was incorporated in an acrylic pressure sensitive adhesive (Duro-Tak 87-2979; National Starch and Chemical, Bridgewater, N.J.) at 98.5% (w/w) (Formula 1-A). Comparable formulations of 1.5% estradiol and 96% adhesive were prepared with 2.5% lauroyl lactylic acid (Formula 1-B) or lauroyl glycolic acid (Formula 1-C), both obtained from R.I.T.A. Corp. (Woodstock, Ill.). The results of in vitro skin permeation experiments using these systems are shown in Table 1a.

In vitro skin permeation experiments were also performed using higher enhancer concentrations. Estradiol at 1.5% (w/w) was incorporated in a pressure sensitive adhesive (Duro-Tak 87-2979) at 98.5% (w/w) (Formula 1-D). Comparable formulations of 1.5% estradiol and 93.5% adhesive were prepared with 5.0% lauroyl lactylic acid (Formula 1-E) or lauroyl glycolic acid (Formula 1-F). The results of in vitro skin permeation experiments using these systems are shown in Table 1b.

TABLE 1a

| | Formula 1-A Unenhanced | Formula 1-B Lauroyl Lactylic Acid | | Formula 1-C Lauroyl Glycolic Acid | |
|---|---|---|---|---|---|
| Skin Source | Q24* μg/cm²/24 h | Q24* μg/cm²/24 h | E† | Q24* μg/cm²/24 h | E† |
| 1-I | 5.3 ± 0.9 (n = 5) | 7.4 ± 0.7 (n = 5) | 1.4 | 10.9 ± 2.9 (n = 5) | 2.1 |
| 1-II | 8.1 ± 2.2 (n = 5) | 11.5 ± 1.5 (n = 5) | 1.4 | 13.5 ± 1.5 (n = 5) | 1.7 |
| 1-III | 5.7 ± 0.6 (n = 5) | 9.5 ± 1.4 (n = 5) | 1.7 | 11.8 ± 2.3 (n = 5) | 2.1 |
| 1-IV | 4.6 ± 0.9 (n = 5) | 6.0 ± 1.5 (n = 5) | 1.3 | 7.9 ± 1.2 (n = 5) | 1.7 |
| All Skins (mean) | 5.9 ± 1.5 | 8.6 ± 2.4 | 1.4 ± 0.1 | 11.0 ± 2.3 | 1.9 ± 0.2 |

*Q24 = Cumulative Drug Delivered in 24 Hours, μg/cm²/24 h.
†E Enhancement Ratio = Q24$_{enhanced}$/Q24$_{unenhanced}$ TABLE 1b

| | Formula 1-D Unenhanced | Formula 1-E Lauroyl Lactylic Acid | | Formula 1-F Lauroyl Glycolic Acid | |
|---|---|---|---|---|---|
| Skin Source | Q24 μg/cm²/24 h | Q24 μg/cm²/24 h | E | Q24 μg/cm²/24 h | E |
| 1-V | 1.7 ± 0.4 (n = 5) | 4.8 ± 0.9 (n = 5) | 2.9 | 7.6 ± 1.4 (n = 5) | 4.5 |
| 1-VI | 7.1 ± 0.6 (n = 5) | 12.1 ± 3.2 (n = 5) | 1.7 | 17.1 ± 2.9 (n = 5) | 2.4 |
| 1-VII | 2.9 ± 1.0 (n = 5) | 5.3 ± 0.7 (n = 5) | 1.9 | 10.3 ± 1.0 (n = 5) | 3.6 |
| 1-VIII | 6.3 ± 2.3 (n = 5) | 13.3 ± 1.8 (n = 5) | 2.1 | 15.4 ± 1.8 (n = 5) | 2.4 |
| All Skins (mean) | 4.5 ± 2.6 | 8.9 ± 4.5 | 2.1 ± 0.5 | 12.6 ± 4.4 | 3.2 ± 1.0 |

As shown in Table 1a, by comparing the average Enhancement Ratios (E), the in vitro permeation of estradiol was increased on average about 2 fold by the addition of the 2.5% lauroyl glycolic acid (Formula 1-C), in contrast to an average increase of only about 1.4 fold by the addition of 2.5% lauroyl lactylic acid (Formula 1-B).

Again, by comparing the average Enhancement Ratios (E), as shown in Table 1b, in vitro permeation of estradiol was increased on average more than 3 fold by the addition of the 5.0% lauroyl glycolic acid (Formula 1-F), in contrast to an average increase of 2 fold by the addition of 5.0% lauroyl lactylic acid (Formula 1-E). These results demonstrate that lauroyl glycolic acid is an unusually effective permeation enhancer when compared to its closest α-hydroxy acid homolog, lauroyl lactylic acid.

EXAMPLE 2

Permeation enhancement of estradiol with lauroyl glycolic acid was compared to permeation enhancement using the known permeation enhancer, lauroyl lactylic acid, in a different adhesive type. Estradiol at 1.5% (w/w) was incorporated in a pressure sensitive adhesive (Duro-Tak 2516; National Starch and Chemical) at 98.5% (w/w) (Formula 2-A). Comparable formulations of 1.5% estradiol and 96.5% adhesive were prepared with 2.0% lauroyl lactylic acid (Formula 2-B) or lauroyl glycolic acid (Formula 2-C). The results of in vitro skin permeation experiments using these systems are shown in Table 2.

TABLE 2

| Skin Source | Formula 2-A Unenhanced Q24 $\mu g/cm^2/24$ h | Formula 2-B Lauroyl Lactylic Acid Q24 $\mu g/cm^2/24$ h | E | Formula 2-C Lauroyl Glycolic Acid Q24 $\mu g/cm^2/24$ h | E |
|---|---|---|---|---|---|
| 2-I | 5.0 ± 1.0 (n = 4) | 7.9 ± 1.9 (n = 4) | 1.6 | 16.6 ± 8.2 (n = 4) | 3.3 |
| 2-II | 4.7 ± 0.7 (n = 4) | 10.0 ± 1.6 (n = 4) | 2.1 | 13.4 ± 1.3 (n = 4) | 2.8 |
| 2-III | 5.0 ± 1.1 (n = 4) | 7.2 ± 1.1 (n = 4) | 1.5 | 11.5 ± 1.0 (n = 4) | 2.3 |
| All Skins (mean) | 4.9 ± 0.2 | 8.4 ± 1.5 | 1.7 ± 0.4 | 13.8 ± 2.6 | 2.8 ± 0.5 |

These results again demonstrate that lauroyl glycolic acid is an unusually effective permeation enhancer when compared to its closest α-hydroxy acid homolog, lauroyl lactylic acid.

EXAMPLE 3

Permeation enhancement using the free acid form of glycolic acid fatty acid esters as permeation enhancer was evaluated using a non-ionic xanthine derivative, propentofylline, as a model compound. Propentofylline at 10.0% (w/w) was incorporated in a pressure sensitive adhesive (TSR, Sekisui Chemical Company, Osaka, Japan) at 90.0% (w/w) (Formulation 3-A). Comparable formulations of 10.0% propentofylline and 85.0% adhesive were prepared with 5.0% lauroyl lactylic acid (Formulation 3-B) and 5.0% lauroyl glycolic acid (Formulation 3-C). The results of in vitro skin permeation experiments using these systems are shown in Table 3.

TABLE 3

| Skin Source | Formula 3-A Unenhanced Q24 $\mu g/cm^2/24$ h | Formula 3-B Lauroyl Lactylic Acid Q24 $\mu g/cm^2/24$ h | E | Formula 3-C Lauroyl Glycolic Acid Q24 $\mu g/cm^2/24$ h | E |
|---|---|---|---|---|---|
| 3-I | 94.1 ± 13.5 (n = 5) | 139.8 ± 23.2 (n = 5) | 1.5 | 199.3 ± 26.3 (n = 5) | 2.1 |
| 3-II | 175.9 ± 37.9 (n = 5) | 272.7 ± 29.7 (n = 5) | 1.6 | 495.1 ± 53.5 (n = 5) | 2.8 |
| 3-III | 440.5 ± 92.1 (n = 5) | 541.0 ± 69.8 (n = 5) | 1.2 | 731.0 ± 117.3 (n = 5) | 1.7 |
| 3-IV | 118.4 ± 20.2 (n = 5) | 162.3 ± 23.8 (n = 5) | 1.4 | 260.8 ± 76.0 (n = 5) | 2.2 |
| All Skins (mean) | 207.2 ± 159.3 | 278.9 ± 184.1 | 1.4 ± 0.1 | 421.5 ± 242.5 | 2.2 ± 0.5 |

As shown by the mean E values in Table 3, in vitro permeation of propentofylline was increased on average over two fold by the addition of 5.0% lauroyl glycolic acid (Formula 3-C), in contrast to an average increase of about 1.4 fold by the addition of 5.0% lauroyl lactylic acid. These results illustrate that acyl glycolic acid esters are an effective permeation enhancer for the class of non-ionic, non-steroidal drugs.

EXAMPLE 4

Permeation enhancement of estradiol with the salt form of lauroyl glycolic acid, sodium lauroyl glycolate, was compared to permeation enhancement using sodium lauroyl lactylate. Estradiol at 1.5% (w/w) was incorporated in a pressure sensitive adhesive (National Starch 2516) at 98.5% (w/w) (Formula 4-A). Comparable formulations of 1.5% estradiol and 96.5% adhesive were prepared with 2.0% sodium lauroyl lactylate (Formula 4-B) or sodium lauroyl glycolate (Formula 4-C) from R.I.T.A. Corporation (Woodstock, Ill.). The results of in vitro skin permeation experiments using these systems are shown in Table 4.

TABLE 4

| Skin Source | Formula 4-A Unenhanced Q24 $\mu g/cm^2/24$ h | Formula 4-B Na Lauroyl Lactylate Q24 $\mu g/cm^2/24$ h | E | Formula 4-C Na Lauroyl Glycolate Q24 $\mu g/cm^2/24$ h | E |
|---|---|---|---|---|---|
| 4-I | 5.0 ± 1.0 (n = 4) | 5.4 ± 0.9 (n = 4) | 1.1 | 11.22 ± 5.0 (n = 4) | 2.3 |
| 4-II | 4.7 ± 0.7 (n = 4) | 6.5 ± 0.8 (n = 4) | 1.4 | 10.1 ± 1.1 (n = 4) | 2.1 |
| 4-III | 5.0 ± 1.1 (n = 4) | 8.2 ± 0.8 (n = 4) | 1.6 | 6.3 ± 0.4 (n = 4) | 1.3 |
| All Skins (mean) | 4.9 ± 0.2 | 6.7 ± 1.4 | 1.4 ± 0.3 | 9.2 ± 2.6 | 1.9 ± 0.5 |

As shown by the mean E values in Table 4, in vitro permeation of estradiol was increased on average about two fold by the addition 2.0% sodium lauroyl glycolate (Formula 4-C), in contrast to an average increase of about 1.4 fold by the addition of 2.0% sodium lauroyl lactylate (Formula 4-B).

EXAMPLE 5

Permeation enhancement using the salt, sodium lauroyl glycolate, was examined using buspirone HCl in an aqueous emulsion based acrylic adhesive matrix as a model system. Buspirone HCl is the pharmaceutically approved salt of the basic drug indicated for the treatment of anxiety disorders. A matrix system without permeation enhancers (Formulation 5-A) was prepared with an acrylic copolymer adhesive (Nacor 72-9965, National Starch and Chemical, Bridgewater, N.J.) and buspirone HCl at a concentration of 1% (w/w). An enhanced formulation was prepared containing 2.5% (w/w) sodium lauroyl glycolate (Formulation 5-B) obtained from R.I.T.A. Corporation (Woodstock, Ill.) Polyvinylpyrrolidone (Kollidon 90, BASF, Parsippanny, N.J.) at 5% (w/w) was added as a thickening agent to aid in matrix film casting. The results of in vitro skin permeation experiments using these systems are shown in Table 5.

TABLE 5

| Skin Source | Formula 5-A Unenhanced Q24 $\mu g/cm^2/24$ h | Formula 5-B Na Lauroyl Glycolate Q24 $\mu g/cm^2/24$ h | E |
|---|---|---|---|
| 5-I | 19 ± 5 (n = 5) | 29 ± 3 (n = 5) | 1.5 |
| 5-II | 7 ± 1 (n = 5) | 10 ± 2 (n = 5) | 1.5 |
| All Skins (mean) | 13 ± 7 (n = 10) | 19 ± 10 (n = 10) | 1.5 ± 0.04 |

As shown by the mean E value in Table 5, sodium lauroyl glycolate increased the permeation of buspirone from the matrix system by on average about 50% as compared to the unenhanced system. The data in this example demonstrates that sodium lauroyl glycolate is an effective permeation enhancer for a basic drug in an aqueous emulsion based acrylic pressure sensitive adhesive.

EXAMPLE 6

Permeation enhancement using the free acid form of an acyl glycolic acid ester as a permeation enhancer was evaluated using a hydroalcoholic gel containing sodium diclofenac as a model compound. Sodium diclofenac at 7.5 mg/ml was incorporated in a hydroalcoholic gel containing 65% (v/v) ethanol (190 proof, USP; Quantum, Cincinnati, Ohio), 35% (v/v) $H_2O$, and 2% (w/v) carbomer (Pemulen TR-1, B.F. Goodrich, Cleveland, Ohio) (Formulation 6-A). Comparable enhanced formulations were prepared of 7.5 mg/ml sodium diclofenac, 65% ethanol (EtOH), 33% $H_2O$, 2% lauroyl glycolic acid (v/v) and 2% carbomer (w/v) (Formulation 6-B). In vitro permeation experiments performed using occluded dosing of these gels are shown in Table 6.

TABLE 6

| Skin Source | Formula 6-A Unenhanced Q24 $\mu g/cm^2/24$ h | Formula 6-B Lauroyl Glycolic Acid Q24 $\mu g/cm^2/24$ h | E |
|---|---|---|---|
| 6-I | 55.8 ± 21.9 (n = 5) | 340.78 ± 95.1 (n = 5) | 6.1 |
| 6-II | 75.5 ± 50.7 (n = 5) | 255.9 ± 56.8 (n = 4) | 3.4 |
| 6-III | 92.5 ± 25.0 (n = 5) | 191.8 ± 41.8 (n = 5) | 2.1 |
| All Skins (means) | 74.6 ± 18.4 | 262.8 ± 74.7 | 3.9 ± 2.0 |

As shown by the mean E value in Table 6, in vitro permeation of sodium diclofenac was increased about fourfold, on the average, by the addition of 2.0% lauroyl glycolic acid (Formula 6-B), relative to the unenhanced system. This illustrates that acyl glycolic acid esters are effective permeation enhancers for the class of acidic drugs. This example further shows that acyl glycolic acid esters can be formulated in gel type formulation suitable for application in reservoir patches (occluded form) or in topically applied free form gels.

EXAMPLE 7

Permeation enhancement using the free acid form of an acyl glycolic acid ester as a permeation enhancer was evaluated using a hydroalcoholic gel containing testosterone as a model compound. Testosterone at 15 mg/ml was incorporated in a hydroalcoholic gel containing 65% EtOH(v/v), 35% $H_2O$ (v/v), and 2% carbomer (w/v) (Pemulen TR-1, B.F. Goodrich, Cleveland, Ohio) (Formulation 7-A). Comparable enhanced formulations were prepared of 15 mg/ml testosterone and 65% EtOH, 33% $H_2O$, 2% lauroyl glycolic acid (v/v), and 2% carbomer (w/v) (Formulation 7-B). The results of permeation experiments conducted with these systems under occluded dosing conditions are summarized in Table 7.

TABLE 7

| Skin Source | Formula 7-A Unenhanced Q24 $\mu g/cm^2/24$ h | Formula 7-B Lauroyl Glycolic Acid Q24 $\mu g/cm^2/24$ h | E |
|---|---|---|---|
| 7-I | 103.8 ± 18.2 (n = 5) | 360.5 ± 54.0 (n = 5) | 3.5 |
| 7-II | 76.2 ± 14.7 (n = 5) | 346.4 ± 59.9 (n = 5) | 4.5 |
| 7-III | 62.9 ± 25.2 (n = 5) | 318.6 ± 56.8 (n = 5) | 5.1 |
| All Skins | 81.0 ± 20.9 | 341.8 ± 21.3 | 4.4 ± 0.8 |

As shown by the mean E values in Table 7, in vitro permeation of testosterone was increased on average of slightly more than four times by the addition of 2.0% lauroyl glycolic acid (Formula 7-B), relative to the unenhanced system. This example illustrates that acyl glycolic acid esters are effective permeation enhancers for steroids in a hydroaloholic gel under occluded dosing conditions.

EXAMPLE 8

Permeation enhancement using the free acid form of an acyl glycolic acid ester as a permeation enhancer was evaluated using testosterone as a model compound in a hydroalcoholic gel loaded on skin an unoccluded thin film. This loading technique is an in vitro model for the free form topical application of a gel or cream. Formulations 7-A and 7-B were prepared as described in Example 7. The results of permeation experiments conducted with these systems under unoccluded thin film application are summarized in Table 8.

TABLE 8

| Skin Source | Formula 8-A Unenhanced Q24 $\mu g/cm^2/24$ h | Formula 8-B Lauroyl Glycolic Acid Q24 $\mu g/cm^2/24$ h | E |
|---|---|---|---|
| 8-I | 1.6 ± 0.5 (n = 5) | 3.5 ± 1.4 (n = 5) | 2.2 |
| 8-II | 4.4 ± 1.8 (n = 5) | 9.0 ± 2.3 (n = 3) | 2.0 |
| 8-III | 6.7 ± 1.4 (n = 4) | 12.8 ± 3.7 (n = 5) | 1.9 |
| All Skins (mean) | 4.2 ± 2.6 | 8.4 ± 4.7 | 2.0 ± 0.2 |

As shown by the mean E value in Table 8, in vitro permeation of testosterone was increased on an average of two-fold by the addition of 2.0% lauroyl glycolic acid (Formula 8-B), relative to the unenhanced system. This example illustrates that acyl glycolic acid esters are effective permeation enhancers when used in a free form topical dosage form such as a gel or cream.

The above examples are but illustrative of drugs or transdermal formulations which may be employed in operation of the present invention. The invention is directed to the discovery that the utilization of fatty acid esters of glycolic acid and its salts as defined above enhances the cumulative amount of drug delivered as compared to unenhanced formulations or through the use of known conventional enhancers. While the certain fatty acids and glycolic acid salts thereof have been primarily used for purposes of illustration other aliphatic esters of glycolic acid and other glycolic acid salts may also be utilized and similar results will be realized. Therefore, specific drugs and/or formulations are not critical as long as they are compatible with the fatty acid esters of glycolic acid and its salts as disclosed herein. Within the guidelines presented herein, a certain amount of experimentation to obtain optimal formulations can be readily carried out by those skilled in the art. Therefore, the invention is limited in scope only by the following claims and functional equivalents thereof.

We claim:

1. A pharmaceutical composition for transdermal application having penetration-enhancing properties comprising:
   (a) a safe and effective amount of an active pharmaceutical permeant contained in,
   (b) a penetration-enhancing system comprising,
      (i) about 0.25 to about 50% by weight of an enhancer consisting of the fatty acid esters of glycolic acid and its salts, represented by the formula:

$$[RCO-(O-CH_2-CO)_aO]_bM$$

where R is a $C_5$ to $C_{21}$ alkyl or alkenyl group which may be either straight or branched chained and which may a contain hydroxy substituents; a is an integer of 1 to 4, b is 1 or 2 and M is H or a pharmaceutically acceptable counterion having a valency of 1 or 2.
      (ii) a pharmaceutically suitable carrier vehicle.

2. A composition according to claim 1 wherein the carrier vehicle comprises a member selected from the group consisting of a biocompatible pressure sensitive adhesive and a fluid of controlled viscosity in which the active permeant and enhancer are homogeneously contained.

3. A composition according to claim 2 wherein M is a member selected from the group consisting of H, Na, K, Ca, Mg and ammonium or amines salts.

4. A composition according to claim 3 wherein the carrier vehicle comprises a pressure sensitive adhesive and wherein the enhancer is present in the penetration enhancing system in an amount ranging from 0.25 to 30% by weight.

5. A composition according to claim 4 wherein the pressure sensitive adhesive is a member selected from the group consisting of acrylic, rubber, SBR, EVA and silicone adhesives.

6. A composition according to claim 5 in the form of a matrix system having an occlusive backing.

7. A composition according to claim 6 wherein the enhancer is lauroyl glycolic acid.

8. A composition according to claim 6 wherein the enhancer is sodium lauroyl glycolate.

9. A composition according to claim 4 wherein the enhancer additionally contains a secondary enhancer and wherein the weight ratio of the fatty acid esters of glycolic acid or acid salt enhancer to secondary enhancer is between about 5:1 to 1:3.

10. A composition according to claim 9 wherein the secondary enhancer is a member selected from the group consisting of methyl laurate, lauryl alcohol, glycerol monolaurate, oleic acid, oleyl alcohol, glycerol monooleate, glycerol dioleate and glycerol trioleate and mixtures thereof.

11. A composition according to claim 3 wherein the carrier vehicle comprises a fluid of controlled viscosity as a continuous phase and wherein the enhancer is present in the penetration enhancing system in an amount ranging from 0.25 to 30% by weight.

12. A composition according to claim 11 wherein the carrier vehicle fluid of controlled viscosity comprises, as a continuous phase, a member selected from the group consisting of water, ethanol, propanol, isopropanol, a gelling agent, glycerin and mixtures thereof.

13. A composition according to claim 12 wherein the carrier vehicle fluid of controlled viscosity is present as a solution, suspension or emulsion and wherein the penetration enhancing system is contained in an occlusive device in the form of a reservoir system for purposes of holding the composition against the skin surface for administration.

14. A composition according to claim 13 wherein the enhancer is lauroyl glycolic acid.

15. A composition according to claim 13 wherein the enhancer is sodium lauroyl glycolate.

16. A composition according to claim 12 wherein the carrier vehicle fluid of controlled viscosity is present as a gel, lotion, cream, paste, or ointment for application to an afflicted situs.

17. A composition according to claim 16 wherein the enhancer is lauroyl glycolic acid.

18. A composition according to claim 16 wherein the enhancer is s odium lauroyl glycolate.

19. A composition according to claim 11 wherein the enhancer additionally contains a secondary enhancer and wherein the weight ratio of the fatty acid esters of glycolic acid or acid salt enhancer to secondary enhancer is between about 5:1 to 1:3.

20. A composition according to claim 19 wherein the secondary enhancer is a member selected from the group consisting of methyl laurate, lauryl alcohol, glycerol monolaurate, oleic acid, oleyl alcohol, glycerol monooleate, glycerol dioleate and glycerol trioleate and mixtures thereof.

21. A method for enhancing the penetration of an active pharmaceutical permeant through the skin of a human or warm-blooded animal which comprises applying to the skin a composition comprising:
   (a) a safe and effective amount of an active pharmaceutical permeant contained in,
   (b) a penetration-enhancing system comprising,
      (I) about 0.25 to about 50% by weight of an enhancer consisting of the fatty acid esters of glycolic acid and its salts represented by the formula:

$$[RCO-(O-CH_2-CO)_aO]_bM$$

where R is a $C_5$ to $C_{21}$ alkyl or alkenyl group which may be either straight or branched chained and which may contain hydroxy substituents; a is an integer of 1 to 4, b is 1 or 2 and M is H or a pharmaceutically acceptable counterion having a valency of 1 or 2.
      (ii) a pharmaceutically suitable carrier vehicle.

22. A method according to claim 21 wherein the carrier vehicle comprises a member selected from the group consisting of a biocompatible pressure sensitive adhesive and a fluid of controlled viscosity in which the active permeant and enhancer are homogeneously contained.

23. A method according to claim 22 wherein M is a member selected from the group consisting of H, Na, K, Ca, Mg and ammonium or amines salts.

24. A method according to claim 23 wherein the carrier vehicle comprises a pressure sensitive adhesive and wherein the enhancer is present in the penetration enhancing system in an amount ranging from 0.25 to 30% by weight.

25. A method according to claim 24 wherein the pressure sensitive adhesive is a member selected from the group consisting of acrylic, rubber, SBR, EVA and silicone adhesives.

26. A method according to claim 25 wherein the composition is applied to an application situs in the form of a matrix system having an occlusive backing.

27. A method according to claim 26 wherein the enhancer is lauroyl glycolic acid.

28. A method according to claim 26 wherein the enhancer is sodium lauroyl glycolate.

29. A method according to claim 24 wherein the enhancer additionally contains a secondary enhancer and wherein the weight ratio of the fatty acid esters of glycolic acid or acid salt enhancer to secondary enhancer is between about 5:1 to 1:3.

30. A method according to claim 29 wherein the secondary enhancer is a member selected from the group consisting of methyl laurate, lauryl alcohol, glycerol monolaurate, oleic acid, oleyl alcohol, glycerol monooleate, glycerol dioleate and glycerol trioleate and mixtures thereof.

31. A method according to claim 23 wherein the carrier vehicle comprises a fluid of controlled viscosity as a continuous phase and wherein the enhancer is present in the penetration enhancing system in an amount ranging from 0.25 to 30% by weight.

32. A method according to claim 31 wherein the carrier vehicle fluid of controlled viscosity comprises, as a continuous phase, a member selected from the group consisting of water, ethanol, propanol, isopropanol, a gelling agent, glycerin and mixtures thereof.

33. A method according to claim 32 wherein the composition is applied to an application situs wherein the carrier vehicle fluid of controlled viscosity is present as a solution, suspension or emulsion and wherein the penetration enhancing system is contained in an occlusive device in the form of a reservoir system for purposes of holding the composition against the skin surface at the application situs for administration.

34. A method according to claim 33 wherein the enhancer is lauroyl glycolic acid.

35. A method according to claim 33 wherein the enhancer is sodium lauroyl glycolate.

36. A method according to claim 32 wherein the composition is applied to an afflicted situs wherein the carrier vehicle fluid of controlled viscosity is present as a gel, lotion, cream, paste, or ointment.

37. A method according to claim 36 wherein the enhancer is lauroyl glycolic acid.

38. A method according to claim 36 wherein the enhancer is sodium lauroyl glycolate.

39. A method according to claim 31 wherein the enhancer additionally contains a secondary enhancer and wherein the weight ratio of the fatty acid esters of glycolic acid or acid salt enhancer to secondary enhancer is between about 5:1 to 1:3.

40. A method according to claim 39 wherein the secondary enhancer is a member selected from the group consisting of methyl laurate, lauryl alcohol, glycerol monolaurate, oleic acid, oleyl alcohol, glycerol monooleate, glycerol dioleate and glycerol trioleate and mixtures thereof.

* * * * *